(12) United States Patent
Ou et al.

(10) Patent No.: US 7,145,051 B2
(45) Date of Patent: Dec. 5, 2006

(54) COMBINED OXYDEHYDROGENATION AND CRACKING CATALYST FOR PRODUCTION OF OLEFINS

(75) Inventors: John Di-Yi Ou, Houston, TX (US); Michael A. Risch, Seabrook, TX (US); Blake J. Aronson, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 71 days.

(21) Appl. No.: 10/104,322

(22) Filed: Mar. 22, 2002

(65) Prior Publication Data

US 2003/0181325 A1    Sep. 25, 2003

(51) Int. Cl.
C07C 4/02 (2006.01)
C07C 5/32 (2006.01)

(52) U.S. Cl. ............ 585/648; 585/649; 585/650; 585/651; 585/653; 585/654; 585/660

(58) Field of Classification Search ......... 585/648, 585/649, 650, 651, 653, 654, 660
See application file for complete search history.

(56) References Cited

U.S. PATENT DOCUMENTS

| | | | |
|---|---|---|---|
| 3,872,148 A | 3/1975 | Umemura et al. | 260/465.3 |
| 4,072,600 A | 2/1978 | Schwartz | 208/120 |
| 4,107,032 A | 8/1978 | Chester | 208/120 |
| 4,137,151 A | 1/1979 | Csicsery | 208/120 |
| 4,208,269 A | 6/1980 | Gladrow et al. | 208/120 |
| 4,368,114 A | 1/1983 | Chester et al. | 208/120 |
| 4,368,346 A | 1/1983 | Eastman | 585/658 |
| 4,451,355 A | 5/1984 | Mitchell et al. | 208/113 |
| 4,466,884 A | 8/1984 | Occelli et al. | 208/120 |
| 4,497,971 A | 2/1985 | Eastman et al. | 585/658 |
| 4,568,790 A | 2/1986 | McCain | 585/658 |
| 4,629,718 A | 12/1986 | Jones et al. | 502/241 |
| 4,777,319 A | 10/1988 | Kung et al. | 585/624 |
| 4,781,816 A | 11/1988 | Lee et al. | 208/120 |
| 4,810,358 A | 3/1989 | Groenenboom | 208/121 |
| 4,835,127 A * | 5/1989 | Eastman et al. | 502/213 |
| 4,861,936 A | 8/1989 | Sofranko et al. | 585/500 |
| 4,912,081 A | 3/1990 | Sofranko et al. | 502/207 |
| 4,940,826 A | 7/1990 | Font Freide et al. | 585/600 |
| 4,957,718 A | 9/1990 | Yoo et al. | 423/244 |
| 5,002,653 A | 3/1991 | Kennedy et al. | 208/118 |
| 5,043,522 A | 8/1991 | Leyshon et al. | 585/651 |
| 5,053,578 A | 10/1991 | Michaels et al. | 585/500 |
| 5,105,052 A | 4/1992 | Font Freide et al. | 585/651 |
| 5,167,795 A * | 12/1992 | Gartside | 208/67 |
| 5,254,779 A | 10/1993 | Mazzocchia et al. | 585/500 |
| 5,258,567 A | 11/1993 | Kerby et al. | 585/654 |
| 5,306,858 A | 4/1994 | Salem et al. | 585/658 |
| 5,365,006 A | 11/1994 | Serrand | 585/501 |
| 5,380,692 A | 1/1995 | Nakatsuji et al. | 502/303 |
| 5,386,074 A | 1/1995 | Durante et al. | 585/658 |
| 5,414,181 A | 5/1995 | Bearden et al. | 585/654 |
| 5,443,807 A | 8/1995 | Tang et al. | 423/247 |
| 5,476,981 A | 12/1995 | Umansky et al. | 585/656 |
| 5,486,284 A | 1/1996 | Degnan et al. | 208/120 |
| 5,527,979 A | 6/1996 | Agaskar et al. | 585/659 |
| 5,530,171 A | 6/1996 | Agaskar et al. | 585/659 |
| 5,550,309 A | 8/1996 | Maunders et al. | 585/654 |
| 5,625,111 A | 4/1997 | Astbury et al. | 585/653 |
| 5,639,929 A | 6/1997 | Bharadwaj et al. | 585/658 |
| 5,670,037 A | 9/1997 | Zaiting et al. | 208/114 |
| 5,846,402 A | 12/1998 | Mandal et al. | 208/113 |
| 5,866,737 A | 2/1999 | Hagemeyer et al. | 585/443 |
| 5,905,180 A | 5/1999 | Yokoyama et al. | 585/658 |
| 6,015,931 A | 1/2000 | Wu et al. | 585/649 |
| 6,130,183 A * | 10/2000 | Herskowitz et al. | 502/349 |
| 6,459,006 B1 | 10/2002 | Ou et al. | 585/454 |

FOREIGN PATENT DOCUMENTS

| | | |
|---|---|---|
| EP | 0 318 808 A2 | 6/1989 |
| EP | 0 921 175 A1 | 6/1999 |
| EP | 0 921 179 A1 | 6/1999 |
| WO | WO 00/16901 A1 | 3/2000 |

OTHER PUBLICATIONS

Abstract, Mizuno et al., "Selective oxidative dehydrogenation of propane at 380° C. by $Cs_{2.5}Cu_{0.08}H_{3.34}PV_3Mo_9O_{40}$ catalyst", Applied Catalysis A: General 146 (1996) pp. L249-L254, Elsevier Science.

* cited by examiner

*Primary Examiner*—Thuan Dinh Dang
(74) *Attorney, Agent, or Firm*—Andrew B. Griffis

(57) ABSTRACT

A catalyst is provided comprising (1) at least one solid acid component, and (2) at least one metal-based component comprised of one or more element from Groups 1–3, one or more element from Groups 4–15 and one or more element from Groups 16 and 17 of the Periodic Table of the Elements. The catalyst is particularly useful in producing light olefins, preferably from paraffins. When used to convert paraffins to light olefins, the catalyst is capable of high paraffin conversion, high olefin yield, and low aromatic yield. Optionally, the catalyst can further comprise at least one of a support and a binder.

19 Claims, No Drawings

COMBINED OXYDEHYDROGENATION AND CRACKING CATALYST FOR PRODUCTION OF OLEFINS

BACKGROUND OF THE INVENTION

1. Field of the Invention

The present invention relates to a novel catalyst composition and its use in cracking hydrocarbons. The catalyst is particularly useful in producing light olefins, preferably from paraffins. When used to convert paraffins to light olefins, the catalyst is capable of high paraffin conversion, high olefin yield, and low aromatic yield.

2. Discussion of Background Information

Current technologies for the production of light olefins, e.g. ethylene, propylene and, optionally, butylenes can be classified into the two categories of thermal cracking (also known as steam cracking) and catalytic cracking. While these technologies have been practiced for many years and are considered the workhorses for light-olefin production, both have disadvantages.

Steam or thermal cracking, a robust technology that does not utilize catalyst, produces the more valuable ethylene as the primary light olefin product. It is particularly suitable for cracking paraffinic feedstocks to light olefins. However, steam cracking is an expensive, complex technology due to required special construction material to sustain high cracking temperatures (~1600° F.) and high energy input. Sulfur addition is required to passivate the furnace metal surfaces on a continuous basis, creating such undesirable side effects as environmental and product contamination. Steam cracking is not considered to be suitable for cracking feeds containing high concentrations of light olefins as it makes high levels of low value heavy by-products due to the more reactive nature of the olefin feeds. In addition, steam cracking makes a relatively low amount of propylene, and, therefore, is not considered suitable for meeting the anticipated growing demand for propylene in the future. Also, steam cracking requires steam dilution to control product selectivity and to maintain an acceptable run length; steam dilution is costly in terms of capital investment and energy consumption.

Current catalytic cracking technologies employ solid acid catalysts such as zeolites to promote cracking reactions. Unlike steam cracking technology, propylene is the primary light olefin product of catalytic cracking. Accordingly, catalytic cracking would be considered as the main source for growing propylene demand. Catalytic cracking (cat cracking) is typically operated at lower temperatures than steam cracking. Also, special treatments such as sulfur injection and special construction materials are not necessary. However, cat cracking also has its drawbacks. Currently, cat cracking mostly operates at less than 1100° F. and can only convert the more expensive and relatively rare olefinic feeds to light olefins. It is not capable of cracking the more cost-effective and more abundant paraffinic feeds to acceptable yields. Paraffins are less reactive than olefins. To achieve significant paraffin conversion, cracking paraffins requires more active catalyst which operates at temperatures greater than 1200° F., which, in turn, requires catalyst regeneration at above 1300° F. To this point in time, there have been no commercially satisfactory catalysts at such severe conditions. Also, by material balance, acid cracking of a paraffin molecule generates a smaller olefin molecule and a smaller paraffin molecule. This is relatively undesirable compared to cracking an olefin molecule, which usually generates two smaller olefin molecules. Consequently, the yield of light olefins from cat cracking of paraffin feeds becomes significantly lower than that from cracking olefins. Furthermore, selectivity to light olefins decreases with increasing temperature. In addition to light paraffins, other by-products such as the relatively lower valued aromatic compounds become significant at temperatures greater than 1200° F. It is also significant that cracking paraffins to light olefins is highly endothermic. How to provide the large amount of heat input into a commercial catalytic reactor at temperatures greater than 1200° F. is an engineering challenge.

U.S. Pat. No. 4,497,971, which is incorporated herein by reference in its entirety, relates to an improved catalytic process for the cracking and oxidative dehydrogenation of light paraffins, and a catalyst therefor. According to this patent, a paraffin or mixtures of paraffins having from 2 to 5 carbon atoms is oxidatively dehydrogenated in the presence of a cobalt-based catalyst composition which not only has oxidative dehydrogenation capabilities but also has the capability to crack paraffins having more than two carbon atoms so that a paraffin such as propane can be converted to ethylene. If the feed to the oxidative dehydrogenation process contains paraffins having more than two carbon atoms, some cracking of such paraffins will occur at the conditions at which the oxidative dehydrogenation process is carried out.

U.S. Pat. No. 4,781,816, which is incorporated herein by reference in its entirety, relates to a catalytic cracking process and to a process for cracking heavy oils. It is an object of the disclosed invention to provide a process for cracking hydrocarbon containing feedstocks, which contain vanadium compounds as impurities. According to this patent, the feedstream to be treated contains at least about 5 wppm vanadium. The catalyst comprises a physical mixture of zeolite embedded in an inorganic refractory matrix material, and at least one oxide of a metal selected from the group consisting of Be, Mg, Ca, Sr, Ba and La (preferably MgO) on a support material comprising silica.

U.S. Pat. No. 5,002,653, which is incorporated herein by reference in its entirety, relates to an improved catalytic cracking process using a catalyst composition for use in the conversion of hydrocarbons to lower-boiling fractions. More particularly, the invention comprises a process for using a dual component catalyst system for fluid catalytic cracking, which catalyst demonstrates vanadium passivation and improved sulfur tolerance. The catalyst comprises a first component comprising a cracking catalyst having high activity, and, a second component, as a separate and distinct entity, the second component comprising a calcium/magnesium-containing material in combination with a magnesium-containing material, wherein the calcium/magnesium-containing compound is active for metals trapping, especially vanadium trapping.

A significant need exists for a cracking technology which overcomes the above-discussed disadvantages of present, commercial cracking technology. It is believed that no catalytic cracking of paraffins is performed commercially at this time.

SUMMARY OF THE INVENTION

One aspect of the present invention relates to a catalyst comprising (1) at least one solid acid component, and (2) at least one metal-based component comprised of one or more element from Groups 1–3, one or more element from Groups 4–15 and one or more element from Groups 16 and 17 of the Periodic Table of the Elements. Optionally, the catalyst can further comprise at least one of a support and a binder.

According to another aspect of the present invention, the solid acid catalyst is in physical admixture with, or chemically bound to, the metal-based component. Preferably, the solid acid component is in physical admixture with the metal-based component. Also, the elements from Groups 1–3, Groups 4–15 and Groups 16 and 17 can be chemically bound, both the elements between and within the groups. For example, it would be within the scope of the present invention for two or more elements from Groups 1–3 to be chemically bound to each other, as well as, chemically bound to the element(s) from Groups 4–15. Preferably, the chemical binding is only between elements of different groups and not between elements within the same group, i.e., two or elements from Groups 1–3 being in physical admixture with each other but chemically bound to the element(s) from Groups 4–15 and/or from Groups 16 and 17.

The solid acid component can comprise at least one of one or more amorphous solid acid, one or more crystalline solid acid and one or more supported acid. In one embodiment of the present invention, the solid acid catalyst comprises at least one molecular sieve. In a preferred embodiment, the molecular sieve comprises at least one of crystalline silicates, crystalline substituted silicates, crystalline aluminosilicates, crystalline substituted aluminosilicates, crystalline aluminophosphates, crystalline substituted aluminophosphates, zeolite-bound-zeolite, having 8- or greater than 8 membered oxygen rings in framework structures. In another embodiment of the present invention, the solid acid component is at least one zeolite. The zeolite can comprise at least one of faujasite and MFI. The faujasite zeolite can be Y zeolite. The MFI zeolite can be ZSM-5 zeolite.

In another aspect of the present invention, the element(s) from Groups 1–3 is (are) at least one of lithium, sodium, potassium, magnesium, calcium, barium, lanthanum, samarium and yttrium. Preferably, the element(s) from Groups 1–3 is (are) at least one of lithium, sodium, magnesium, calcium, lanthanum and samarium. Magnesium and calcium are more preferred. Most preferably, the element(s) from Groups 1–3 is magnesium.

In another aspect of the present invention, preferably, the element(s) from Groups 4–15 is (are) at least one of vanadium, titanium, chromium, manganese, iron, cobalt, nickel, copper, zinc, zirconium, molybdenum, cadmium, hafnium, tantalum, tungsten, osmium, niobium, iridium, bismuth and platinum. More preferably, the element(s) from Groups 4–15 is (are) at least one of vanadium, titanium, niobium and manganese. Most preferably, the element from Groups 4–15 is vanadium.

In another aspect of the invention, preferably, the element(s) from Groups 16 and 17 is (are) at least one of oxygen, fluorine, sulfur, chlorine, bromine and iodine. More preferably, the element(s) from Groups 16 and 17 is (are) at least one of sulfur and oxygen. Most preferably, the element from Groups 16 and 17 is oxygen.

The weight ratio of solid acid component to the total weight of metal oxides and transition metal oxides can be about 99:1 to 1:99. Preferably, this ratio is about 90:10 to 10:90. Most preferably, this ratio is about 80:20 to 20:80.

The present invention also relates to a catalyst comprised of a dehydrogenation component and a hydrocarbon cracking component, which catalyst, upon contact with a hydrocarbon feedstream, simultaneously cracks the hydrocarbon and generates heat. Preferably, the dehydrogenation component is an oxydehydrogenation (oxidative dehydrogenation) component. Preferably, upon contact with a hydrocarbon feedstream, the catalyst simultaneously dehydrogenates the hydrocarbon and generates heat and cracks the dehydrogenated hydrocarbon to olefins, more preferably to light olefins.

According to another aspect of the present invention, a process comprises contacting a paraffinic hydrocarbon feedstream with a dehygrogenation/cracking catalyst under suitable catalytic reaction conditions to produce olefin, wherein the paraffinic hydrocarbon feedstream is fed to the dehygrogenation/cracking catalyst at a rate of at least 1 million kilograms per day. It is believed that the inventive catalyst is unique in that, among other things, it permits catalytic cracking of paraffins to light olefins in commercial quantities. The conversion of paraffins is preferably at least about 10%. Under cracking conditions which are such as to produce aromatics, the aromatic selectivity is preferably less than 50%. The olefin yield is preferably at least about 5%.

In a further aspect of the present invention, a catalytic cracking process comprises contacting a paraffinic hydrocarbon feedstream with a catalyst comprising a dehydrogenatio/cracking catalyst under suitable catalytic dehydrogenation/cracking conditions to produce olefin, wherein the catalytic dehydrogenation/cracking is conducted in the substantial absence of added heat. Preferably, less than 90% of the total required heat input is added. More preferably, less than 80% of the total required heat input is added. Most preferably, less than 70% of the total required heat input is added.

Another aspect of the present invention relates to a process for treating a hydrocarbon feedstream comprising contacting the feedstream under dehydrogenation/cracking conditions with a catalyst comprising (1) at least one solid acid component, and (2) at least one metal-based component comprised of one or more element from Groups 1–3, one or more element from Groups 4–15 and one or more element from Groups 16 and 17 of the Periodic Table of the Elements.

Preferably, the hydrocarbon feedstream is simultaneously dehydrogenated and cracked. The dehydrogenation preferably comprises oxydehydrogenation (oxidative dehydrogenation). More preferably, the oxydehydrogenation produces water as a by-product.

The hydrocarbon feedstream can comprise at least one of paraffins, olefins and aromatics. Preferably, the hydrocarbon feedstream comprises paraffins.

The process preferably is conducted in a fixed-bed, moving bed, downer- or riser-reactor. Preferably, the reactor comprises at least one catalyst regenerator. The process can be conducted with, in addition to the hydrocarbon feedstream, a co-feed of free-oxygen containing gas, including pure oxygen and air. Preferably, the process is conducted in an anaerobic manner, that is without the co-feed of free-oxygen containing gas into the reaction vessel(s). More preferably, the anaerobic oxydehydrogenation is conducted using the lattice oxygen in the catalyst as the oxygen source and at least one regenerator is used to reactivate the spent catalyst and to replenish the consumed lattice oxygen.

The process temperature can be from 300–800° C. The process pressure can be from 1–10 atmospheres. The residence time can be from 0.1 to 10 hours. The catalyst to oil ratio is, preferably, from 0.01 to 1000.

In a preferred process, catalyst which has been partially deactivated is contacted with steam. The steam-treated catalyst is reactivated, preferably, by treatment with air. The reactivation temperature is, preferably, from 400–800° C. and the pressure from 1 to 10 atmospheres.

Preferably, the hydrocarbon feedstream comprises paraffinic hydrocarbon which produces light olefins. In addition, in a preferred process, the vanadium content of the feedstream is less than 5 ppm by weight (5 wppm), more preferably less than 0.2 wppm.

DETAILED DESCRIPTION OF THE INVENTION

Unless otherwise stated, all percentages, parts, ratios, etc., are by weight.

Unless otherwise stated, certain terms used herein shall have the following meaning (the following expressions are intended to be interpreted in a non-limiting sense and are intended for purposes of illustration and example): "paraffins" means compounds having no carbon—carbon double bonds and either the formula $C_nH_{2n+2}$ or $C_nH_{2n}$, where n is an integer. "paraffinic feedstream" means hydrocarbon feedstream containing some amount of paraffins but no olefins. "olefins" means non-aromatic hydrocarbons having one or more carbon—carbon double bonds. "light olefins" means ethylene, propylene, and, optionally, butylenes. "catalyst to oil ratio" means the relative amount of catalyst to hydrocarbon by weight. "aromatics" means compounds having one or more than one benzene ring. "physical admixture" means a combination of two or more components obtained by mechanical (i.e., non-chemical) means. "chemically bound" means bound via atom to atom bonds. "dehydrogenation/cracking" means both dehydrogenation reaction and cracking reaction. "dehydrogenation/cracking catalyst" means a catalyst capable of promoting both dehydrogenation reaction and cracking reaction. "simultaneous" means any degree of temporal overlap.

Unless otherwise stated, a reference to an element, compound or component includes the element, compound or component by itself, as well as in combination with other elements, compounds or components, such as mixtures of compounds.

Further, when an amount, concentration, or other value or parameter is given as a list of upper preferable values and lower preferable values, this is to be understood as specifically disclosing all ranges formed from any pair of an upper preferred value and a lower preferred value, regardless of whether ranges are separately disclosed.

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description making apparent to those skilled in the art how the several forms of the present invention may be embodied in practice.

The present invention relates to a catalyst for treating a hydrocarbon feedstream. Such feedstream could comprise, by way of non-limiting example, steam cracked gas oil and residues, gas oils, heating oil, jet fuel, diesel, kerosene, gasoline, coker naphtha, steam cracked naphtha, catalytically cracked naphtha, hydrocrackate, reformate, raffinate reformate, Fischer-Tropsch liquids, Fischer-Tropsch gases, natural gasoline, distillate, virgin naphtha, $C_{5+}$ olefins (i.e., $C_5$ olefins and above), $C_{5+}$ paraffins, ethane, propane, butanes, butenes and butadiene. The present invention is particularly useful for catalytically cracking olefinic and paraffinic feeds to light olefins. Non-limiting examples of olefinic feeds are cat-cracked naptha, coker naptha, steam cracked gas oil, and olefinic Fischer-Tropsch liquids. Non-limiting examples of paraffinic feeds are virgin naptha, natural gasoline, reformate and raffinate. The preferred feedstream is a paraffin feedstream. The preferred products produced are $C_2$ and $C_3$ olefins, and, optionally $C_4$ olefins, i.e., ethylene, propylene, and, optionally, butylenes.

The catalyst of the present invention comprises (1) at least one solid acid component, and (2) at least one metal-based component comprised of one or more element from Groups 1–3, one or more element from Groups 4–15 and one or more element from Groups 16 and 17 of the Periodic Table of the Elements. The two components of the catalyst can be present as either a physical admixture or chemically bound. Preferably, the elements of the metal-based component are chemically bound.

The solid acid component is described by the Brønsted and Lewis definitions as any material capable of donating a proton or accepting an electron pair. This description can be found in K. Tanabe. *Solid Acids and Bases: their catalytic properties*. Tokyo: Kodansha Scientific, 1970, p. 1–2. This reference is incorporated herein by reference in its entirety. The solid acid component can comprise at least one of solid acid, supported acid, or mixtures thereof. The solid acid component can comprise nonporous, microporous, mesoporous, macroporous or as a mixture thereof. These porosity designations are IUPAC conventions and are defined in K. S. W. Sing, D. H. Everett, R. A. W. Haul L. Moscou, R. A. Pierotti, J. Rouquérol, T. Siemieniewska, *Pure&Appl. Chem.* 1995, 57(4), pp. 603–619, which is incorporated herein by reference in its entirety.

Non-limiting examples of solid acid components are natural clays such as kaolinite, bentonite, attapulgite, montmorillonite, clarit, fuller's earth, cation exhange resins and $SiO_2.Al_2O_3$, $B_2O_3.Al_2O_3$, $Cr_2O_3.Al_2O_3$, $MoO_3.Al_2O_3$, $ZrO_2.SiO_2$, $Ga_2O_3.SiO_2$, $BeO.SiO_2$, $MgO.SiO_2$, $CaO.SiO_2$, $SrO.SiO_2$, $Y_2O_3.SiO_2$, $La_2O_3.SiO_2$, $SnO.SiO_2$, $PbO.SiO_2$, $MoO_3.Fe_2(MoO_4)_3$, $MgO.B_2O3$, $TiO_2.ZnO$, $ZnO$, $Al_2O_3$, $TiO_2$, $CeO_2$, $As_2O_3$, $V_2O_5$, $SiO_2$, $Cr_2O_3$, $MoO_3$, $ZnS$, $CaS$, $CaSO_4$, $MnSO_4$, $NiSO_4$, $CuSO_4$, $CoSO_4$, $CdSO_4$, $SrSO_4$, $ZnSO_4$, $MgSO_4$, $FeSO_4$, $BaSO_4$, $KHSO_4$, $K_2SO_4$, $(NH_4)_2SO_4$, $Al_2(SO_4)_3$, $Fe_2(SO_4)_3$, $Cr_2(SO_4)_3$, $Ca(NO_3)_2$, $Bi(NO_3)$, $Zn(NO_3)_2$, $Fe(NO_3)_3$, $CaCO_3$, $BPO_4$, $FePO_4$, $CrPO_4$, $Ti_3(PO_4)_4$, $Zr_3(PO_4)_4$, $Cu_3(PO_4)_2$, $Ni_3(PO_4)_2$, $AlPO_4$, $Zn_3(PO_4)_2$, $Mg_3(PO_4)_2$, $AlCl_3$, $TiCl_3$, $CaCl_2$, $AgCl_2$, $CuCl$, $SnCl_2$, $CaF_2$, $BaF_2$, $AgClO_4$, and $Mg(ClO_4)_2$. Depending on the synthesis conditions, these materials can be prepared as nonporous, microporous, mesoporous, or macroporuous, as defined in the reference cited above. Conditions necessary to these preparations are known to those of ordinary skill in the art.

Non-limiting examples of solid acids can also include both natural and synthetic molecular sieves. Molecular sieves have silicate-based structures ("zeolites") and AlPO-based structures. Some zeolites are silicate-based materials which are comprised of a silica lattice and, optionally, alumina combined with exchangeable cations such as alkali or alkaline earth metal ions. For example, faujasites, mordenites and pentasils are non-limiting illustrative examples of such silicate-based zeolites. Silicate-based zeolites are made of alternating $SiO_2$ and $MO_x$ tetrahedral, where in the formula M is an element selected from Groups 1 through 16 of the Periodic Table (new IUPAC). These types of zeolites have 8-, 10- or 12-membered ring zeolites, such as ZSM-5, ZSM-22, ZSM-48 and ZSM-57.

Other silicate-based materials suitable for use in practicing the present invention include zeolite bound zeolites as described in WO 97/45387, incorporated herein by reference in its entirety. These materials comprise first crystals of an acidic intermediate pore size first zeolite and a binder comprising second crystals of a second zeolite. Unlike zeolites bound with amorphous material such as silica or alumina to enhance the mechanical strength of the zeolite, the zeolite bound zeolite catalyst does not contain significant amounts of non-zeolitic binders.

The first zeolite used in the zeolite bound zeolite catalyst is an intermediate pore size zeolite. Intermediate pore size zeolites have a pore size of from about 5 to about 7 Å and include, for example, AEL, MFI, MEL, MFS, MEI, MTW, EUO, MTT, HEU, FER, and TON structure type zeolites. These zeolites are described in *Atlas of Zeolite Structure Types*, eds. W. H. Meier and D. H. Olson, Butterworth-Heineman, Third Edition, 1992, which is incorporated herein by reference. Non-limiting, illustrative examples of specific intermediate pore size zeolites are ZSM-5, ZSM-11, ZSM-12, ZSM-22, ZSM-23, ZSM-34, ZSM-35, ZSM-38, ZSM-48, ZSM-50 AND ZSM-57. Preferred first zeolites are galliumsilicate zeolites having an MFI structure and alumiminosilicate zeolites having an MFR structure.

The second zeolite used in the zeolite bound zeolite structure will usually have an intermediate pore size (e.g., about 5.0 to about 5.5 Å) and have less activity than the first zeolite. Preferably, the second zeolite will be substantially non-acidic and will have the same structure type as the first zeolite. The preferred second zeolites are aluminosilicate zeolites having a silica to alumina mole ratio greater than 100 such as low acidity ZSM-5. If the second zeolite is an aluminosilicate zeolite, the second zeolite will generally have a silica to alumina mole ratio greater than 100:1, e.g., 500:1; 1,000:1, etc., and in some applications will contain no more than trace amounts of alumina. The second zeolite can also be silicalite, i.e., a MFI type substantially free of alumina, or silicalite 2, a MEL type substantially free of alumina. The second zeolite is usually present in the zeolite bound zeolite catalyst in an amount in the range of from about 10% to 60% by weight based on the weight of the first zeolite and, more preferably, from about 20% to about 50% by weight.

The second zeolite crystals preferably have a smaller size than the first zeolite crystals and more preferably will have an average particle size from about 0.1 to about 0.5 microns. The second zeolite crystals, in addition to binding the first zeolite particles and maximizing the performance of the catalyst will preferably intergrow and form an overgrowth which coats or partially coats the first zeolite crystals. Preferably, the crystals will be resistant to attrition.

The zeolite bound zeolite catalyst is preferably prepared by a three step procedure. The first step involves the synthesis of the first zeolite crystals prior to converting it to the zeolite bound zeolite catalyst. Next, a silica-bound aluminosilicate zeolite can be prepared preferably by mixing a mixture comprising the aluminosilicate crystals, a silica gel or sol, water and optionally an extrusion aid and, optionally, a metal component until a homogeneous composition in the form of an extrudable paste develops. The final step is the conversion of the silica present in the silica-bound catalyst to a second zeolite which serves to bind the first zeolite crystals together.

It is to be understood that the above description of zeolite bound zeolites can be equally applied to non-zeolitic molecular sieves (i.e., AlPO's).

Other molecular sieve materials suitable for this invention include aluminophosphate-based materials. Aluminophosphate-based materials are made of alternating AlO4 and PO4 tetrahedra. Members of this family have 8- (e.g., $AlPO_4$-12, -17, -21, -25, -34, -42, etc.) 10- (e.g., $AlPO_4$-11, 41, etc.), or 12($AlPO_4$5,-31 etc.) membered oxygen ring channels. Although $AlPO_4$s are neutral, substitution of Al and/or P by cations with lower charge introduces a negative charge in the framework, which is countered by cations imparting acidity.

By turn, substitution of silicon for P and/or a P—Al pair turns the neutral binary composition (i.e., Al, P) into a series of acidic-ternary-composition (Si, Al, P) based SAPO materials, such as SAPO-5, -11, -14, -17, -18, -20, -31, -34, -41, -46, etc. Acidic ternary compositions can also be created by substituting divalent metal ions for aluminum, generating the MeAPO materials. Me is a metal ion which can be selected from the group consisting of, but not limited to Mg, Co, Fe, Zn and the like. Acidic materials such as MgAPO (magnesium substituted), CoAPO (cobalt substituted), FeAPO (iron substituted), MnAPO (manganese substituted) ZnAPO (zinc substituted) etc. belong to this category. Substitution can also create acidic quaternary-composition based materials such as the MeAPSO series, including FeAPSO (Fe, Al, P, and Si), MgAPSO (Mg, Al, P, Si), MnAPSO, CoAPSO, ZnAPSO (Zn, Al, P, Si), etc. Other substituted aluminophosphate-based materials include ElAPO and ElAPSO (where El=B, As, Be, Ga, Ge, Li, Ti, etc.). As mentioned above, these materials have the appropriate acidic strength for reactions such as cracking. The more preferred aluminophosphate-based materials include 10- and 12-membered ring materials (SAPO-11, -31, -41; MeAPO-11, -31, -41; MeAPSO-11, -31, -41; ElAPO-11, -31, -41; ElAPSO-11, -31, -41, etc.) which have significant olefin selectivity due to their channel structure.

Supported acid materials are either crystalline or amorphous materials, which may or may not be themselves acidic, modified to increase the acid sites on the surface. Non-limiting, illustrative examples are $H_2SO_4$, $H_3PO_4$, $H_3BO_3$, $CH_2(COOH)_2$, mounted on silica, quartz, sand, alumina or diatomaceous earth, as well as heteropoly acids mounted on silica, quartz, sand, alumina or diatomaceous earth. Non-limiting, illustrative examples of crystalline supported acid materials are acid-treated molecular sieves, sulfated zirconia, tungstated zirconia, phosphated zirconia and phosphated niobia.

Although the term "zeolites" includes materials containing silica and optionally, alumina, it is recognized that the silica and alumina portions may be replaced in whole or in part with other oxides. For example, germanium oxide, tin oxide, phosphorus oxide, and mixtures thereof can replace the silica portion. Boron, oxide, iron oxide, gallium oxide, indium oxide, and mixtures thereof can replace the alumina portion. Accordingly, "zeolite" as used herein, means not only materials containing silicon and, optionally, aluminum atoms in the crystalline lattice structure thereof, but also materials which contain suitable replacement atoms for such silicon and aluminum, such as gallosilicates, borosilicates, ferrosilicates, and the like.

Besides encompassing the materials discussed above, "zeolites" also encompasses aluminophosphate-based materials.

Mesoporous solid acids can be ordered and/or non-ordered. Non-limiting examples of ordered mesoporous materials include pillared layered clays (PILC's), MCM-41 and MCM-48. Non-limiting examples of non-ordered mesoporous materials include silica and titania-based xerogels and aerogels.

The solid acid component can also include ordered mesoporous amorphous materials. Non-limiting examples of ordered mesoporous materials include pillared layered clays (PILC's), MCM-41 and MCM-48.

The metal-based component of catalysts in accordance with the present invention is comprised of one or more element from Groups 1–3, one or more element from Groups 4–15 and one or more element from Groups 16 and 17 of the Periodic Table of the Elements. It is intended that reference to an element from each of the noted Groups would include mixtures of elements from the respective groups. For example, reference to one or more element from Groups 1–3 includes a mixture of elements from Groups 1–3 of the Periodic Table.

The metal-based component could be prepared, by way of non-limiting example, by combining salts or chalcogenides (compounds of the Group 16 elements) containing the desired parts through such means as evaporation or precipitation, followed by calcination. The solid acid component is then physically mixed or chemically reacted with the metal-based component and, optionally, combined with the binder to form catalyst particles.

The preparation of the metal-based component and solid-acid component are known to those of ordinary skill in the art. The metal-based component can be obtained through chemical means, such as the combination of metal salts and/or chalcogenides, in solution or slurry, followed by removal of the solvent or mother liquor via evaporation or filtration and drying. The metal-based component can then be ground and calcined. The solid acid and metal-based components can be physically admixed by mechanical mixing.

The element(s) from Groups 1–3 can be any element or a mixture of elements from Groups 1–3 of the Periodic Table of the Elements. It is noted that rare earth elements are to be included as Group 3 elements. In any event, the element(s) from Groups 1–3 is (are) at least one of lithium, sodium, potassium, magnesium, calcium, barium, lanthanum, samarium and yttrium. Preferably, the element(s) from Groups 1–3 is (are) at least one of lithium, sodium, magnesium, calcium, lanthanum and samarium. Magnesium and calcium are more preferred. Most preferably, the element from Groups 1–3 is magnesium.

The element(s) from Groups 4–15 can be any element or a mixture of elements from Groups 4–15 of the Periodic Table of the Elements. Preferably, the element(s) from Groups 4–15 is (are) at least one of vanadium, titanium, chromium, manganese, iron, cobalt, nickel, copper, zinc, zirconium, molybdenum, cadmium, hafnium, tantalum, tungsten, osmium, niobium, iridium, bismuth and platinum. More preferably, the element(s) from Groups 4–15 is (are) at least one of vanadium, titanium, niobium and manganese. Most preferably, the element from Groups 4–15 is vanadium.

The element(s) from Groups 16 and 17 can be any element or a mixture of elements from Groups 16 and 17 of the Periodic Table of the Elements. Preferably, the element(s) from Groups 16 and 17 is (are) at least one of oxygen, fluorine, sulfur, chlorine, bromine and iodine. More preferably, the element(s) from Groups 16 and 17 is (are) at least one of sulfur and oxygen. Most preferably, the element from Groups 16 and 17 is oxygen.

The catalyst described herein can also comprise at least one of a support and a binder. Non-limiting examples of these materials include refractory oxides such as $SiO_2$, $Al_2O_3$, $TiO_2$, $ZrO_2$, aluminum phosphate and mixtures thereof as well as clays such as kaolinite, bentonite, attapulgite, montmorillonite, clarit, fuller's earth and diatomaceous earth. The weight ratio of the catalyst to the support and binder material can be about 99:1 to 1:99.

The catalyst of the present invention is multifunctional in that it can both dehydrogenate and crack a hydrocarbon feedstream. The metal-based component of the catalyst performs the (oxy)dehydrogenation function and the solid acid component performs the cracking function. The catalyst is particularly well-suited for cracking olefinic and paraffinic feeds to light olefins. Commercial olefinic feeds are typically mixtures of olefins and paraffins. Conventional catalytic dehydrogenation/cracking can crack only the olefin portion of the feed to light olefins. The catalysts of the present invention can crack both the olefin and paraffin portions of these feeds thereby increasing the yield for light olefins.

In accordance with the present invention, a catalyst comprises a dehydrogenation component and a hydrocarbon cracking component, which catalyst, upon contact with a hydrocarbon feedstream, simultaneously dehydrogenates and cracks the hydrocarbon. It is preferred that dehydrogenation is conducted via a oxydehydrogenation mechanism which is related to the use of oxygen to promote paraffin dehydrogenation.

Oxydehydrogenation could overcome the engineering challenge of having to supply from an external source a large amount of heat for paraffin cracking. The combustion of hydrogen is highly exothermic and, therefore, would be an ideal internal source of heat supply. This could greatly reduce or even eliminate the need for external heat.

Thus, in accordance with the present invention, a catalytic cracking process comprises contacting a paraffinic hydrocarbon feedstream with a catalyst comprising a dehydrogenation/cracking catalyst under suitable catalytic dehydrogenation/cracking conditions to produce olefin, wherein the catalytic cracking is conducted in the substantial absence of added heat. "Substantial absence of heat" is meant that less than 90% of the total required heat input is added. More preferably, less than 80% of the total required heat input is added. Most preferably, less than 70% of the total required heat input is added. Since cracking reactions are endothermic, the required heat input is simply the overall enthalpy of the reaction. Thus, it is within the skill of one of ordinary skill in the art to calculate the required heat input.

In accordance with the present invention, a free-oxygen containing gas such as air or pure oxygen can be used as the source of oxygen for the oxydehydrogenation reaction. The free-oxygen containing gas can be co-fed into the reaction vessel(s) with the hydrocarbon feedstream. Preferably, the lattice oxygen in the catalyst is used as the source of oxygen for the oxydehydrogenation reaction (anaerobic oxydehydrogenation). Higher dehydrogenation selectivity and less $CO_x$ by-product are achievable using this approach as compared to co-feeding oxygen to the reactor. Using continuous catalyst regeneration technology would overcome the potential problem related to lattice oxygen being quickly consumed with resultant loss of catalyst activity.

The inventive process can be performed using any known reactor. By way of non-limiting, illustrative example, fixed-bed reactors with catalyst regeneration, moving bed reactors with catalyst regeneration such as the continuous catalyst regeneration reactor (also known as CCR), fluidized-bed processes such as a riser reactor with catalyst regeneration and the like would be suitable. A non-limiting illustrative example of a suitable fixed-bed catalyst regeneration system is illustrated in U.S. Pat. No. 5,059,738 to Beech, Jr. et al, which is incorporated herein by reference in its entirety. A non-limiting illustrative example of a suitable continuous catalyst regeneration moving bed reactor is illustrated in U.S. Pat. No. 5,935,415 to Haizmann et al, which is incorporated herein by reference in its entirety. A preferred reactor system would be a downer-regenerator or a riser-regenerator system as described below for illustration purposes only. A riser-regenerator system that would be suitable for use in practicing the inventive process is disclosed in U.S. Pat. No. 5,002,653, which is incorporated herein by reference in its entirety.

In a riser-regenerator system, pre-heated hydrocarbon feed is contacted with catalyst in a feed riser line wherein the reaction primarily takes place. The temperature and pressure for the riser/reactor can be in the range of 300–800° C. and 1–10 atmospheres, respectively. The catalyst to hydrocarbon feed ratio, weight basis, can be in the range of 0.01 to 1000. The residence time in the reaction zone can be in the range of 0.1 second to 10 hours. As the reactions progress, the catalyst is progressively deactivated due to a number of reasons including the consumption of lattice oxygen and the formation of coke on the catalyst surface. The catalyst and hydrocarbon vapors are separated mechanically and hydrocarbons remaining on the catalyst are removed by steam stripping before the catalyst enters a catalyst regenerator. The hydrocarbon vapors are taken overhead to a series of fractionation towers for product separation. Spent catalyst is reactivated in the regenerator by burning off coke deposits with air. The coke burn also serves as an oxidation treatment to replenish the catalyst's lattice oxygen consumed in the reactor. The temperature and pressure for the regenerator can be in the range of 400–800° C. and 1–10 atmospheres, respectively. As required, a small amount of fresh make-up catalyst can be added to the reactor.

Catalytic cracking of paraffinic feeds is not practiced commercially today, not only because of the above-discussed problems related to providing heat to the reactor. There is also a problem related to the low yield of product. Using catalyst in accordance with the present invention, much higher propylene purities are achievable. The above-discussed drawbacks related to typical catalysts and typical catalytic cracking technology are significant reasons for the lack of commercial scale catalytic cracking of paraffins today.

One of the many benefits of the present invention relates to the ability to catalytic crack paraffins to light olefins with high light-olefin yields, high paraffin conversion and low aromatic yield. Thus, in accordance with the present invention, a process comprises contacting a paraffinic hydrocarbon feedstream with a dehydrogenation/cracking catalyst under suitable catalytic dehydrogenation/cracking conditions to produce olefin, preferably light-olefins, wherein the paraffinic hydrocarbon feedstream is fed to the dehydrogenation/cracking at a rate of at least 1 million kilograms per day. The preferred feed rate is at least 2 million kilogram per day. It is even more preferred that the feed rate be at least 3 million kilogram per day. Also, the olefin yield can be at least about 5%. Preferably, the olefin yield is at least about 10%. Most preferably, the olefin yield is at least about 15%. In such process, the paraffin conversion can be at least about 10%. Preferably, the paraffin conversion is at least about 15%. Most preferably, the paraffin conversion is at least about 20%. When the cracking conditions are such as to produce aromatics, the aromatic yield is less than about 50%. Preferably, the aromatic yield is less than about 45%. Most preferably, the aromatic yield is less than about 40%.

In accordance with the present invention, the weight ratio of solid acid component to the total weight of metal-based component is from 99:1 to 1:99. More preferably, the ratio is from 90:10 to 10:90. Most preferably, the ratio is from 85:15 to 15:85.

EXAMPLES

The invention is illustrated in the following non-limiting examples, which are provided for the purpose of representation, and are not to be construed as limiting the scope of the invention. All temperatures are set forth uncorrected in degrees Celsius and all parts and percentages in the examples are by weight unless indicated otherwise.

Example 1

This example illustrates the preparation of catalysts containing a metal-based component and a solid acid component. The V/Mg metal oxide component was prepared by wet impregnation of calcined MgO with $NH_4VO_3$ (Alfa Aesar, Ward Hill, Mass.). A common batch for the V/Mg series was prepared by calcination of 72.5 grams (g) of $Mg(OH)_2$ (Fluka Chemie AG, Buchs, Switzerland) for three hours at 700° C. For each metal-based component, 10 g of the calcined MgO was combined with a solution of ammonium vanadate (Aldrich Chemical Company, Milwaukee, Wis.) and distilled and deionized water (DDI $H_2O$) based on the amounts listed in Table 1.

TABLE 1

| Component D | $V_2O_5$, wt % | $NH_4VO_3$, grams | DD $H_2O$, milliliters | 28–30 wt % $NH_4OH$ added, grams |
|---|---|---|---|---|
| A | 10 | 1.43 | 70 | 1.5 |
| B | 30 | 5.50 | 210 | 5.7 |
| C | 50 | 12.86 | 350 | 12.9 |

The resulting slurry was well mixed and then heated to 80° C. under continued stirring until it was dry. The dried catalysts were then heated to 600° C. for six hours and at 700° C. for another six hours.

The zeolitic component was prepared in some cases by modification of as-received catalysts. OlefinsMax™ (Grace Davison Division of W. R. Grace & Co.) was steamed at 816° C. for 16 hours. SAPO-34 zeolite (obtained from UOP) zeolite was dried at 150° C. for 30 minutes and calcined at 650° C. for 2 hours. SAPO-11 zeolite (obtained from UOP) was utilized in its as received calcined form. Combined catalysts were prepared by physically mixing ground powders of the V/Mg metal oxide and the zeolite or zeolite-containing catalyst. Powders of 3.0 grams of the V/Mg metal oxides and 3.0 grams of the zeolite or zeolite-containing catalyst were mixed thoroughly. The mixed catalyst powders were pelletized and screened to 60–100 mesh particles.

Example 2

This example illustrates the superior performance for ethylene and propylene production from a catalyst consisting of a metal-based component and a solid acid component. The oxydehydrogenation/cracking of n-butane was studied in a downflow, fixed-bed, pulse-type reactor at 550° C. Three catalysts were tested. The first was a 1.0-gram sample of Component C from Example 1. The second was a 1.0-gram sample of steamed OlefinMax prepared in Example 1. The third was a mixture of 1.0 gram Component C and 1.0 gram OlefinMax as described in Example 1. Each catalyst was mixed with SiC to obtain a constant bed height and was pretreated in a helium stream at a flow rate of 50 cc/min for thirty minutes at 550° C. and one atmosphere prior to reaction. At the start of the reaction, the helium flow was sent to a bypass and a pulse of 0.5 g of n-butane flowing at a rate of 50 cc/min was introduced into the system. Once the 0.5 g of n-butane was delivered, the helium flow was redirected to the reactor system. The pressure during reaction was 4–5 psig. Reaction products were analyzed using an on-line gas chromatograph (GC). Table 2 shows the results of three separate tests.

In a particularly preferred process, Component B in combination with a zeolite as described in this Example 1, is used to contact a C5–C11 paraffin stream in a fluidized bed riser reactor.

TABLE 2

| (CWT %)[1] | Component C (1 g) | Component C (1 g) 1 g OlefinsMax | OlefinsMax (1 g) |
|---|---|---|---|
| $C_4$ conversion | 15.79 | 26.43 | 9.58 |
| $C_4^=$ yield | 4.97 | 3.97 | 1.90 |
| $C_4^{==}$ yield | 4.65 | 0.06 | 0.02 |
| CO yield | 0.72 | 0.61 | 0.03 |
| $CO_2$ yield | 2.83 | 2.08 | 0.07 |
| $C_1$ yield | 0.36 | 1.42 | 0.83 |
| $C_2^=$ yield | 0.50 | 3.94 | 1.57 |
| $C_2$ yield | 0.25 | 2.65 | 1.53 |
| $C_3^=$ yield | 0.85 | 5.65 | 2.20 |
| $C_3$ yield | 0.03 | 2.57 | 0.99 |
| Benzene yield | 0.10 | 0.84 | 0.02 |
| Toluene yield | 0.01 | 1.34 | 0.06 |
| $C_{5+}$ (non-arom) | 0.51 | 1.32 | 0.37 |
| $C_4^=$ selectivity | 31.49 | 15.01 | 19.87 |
| $C_4^{==}$ selectivity | 29.46 | 0.23 | 0.16 |
| CO selectivity | 4.56 | 2.30 | 0.28 |
| $CO_2$ selectivity | 17.90 | 7.85 | 0.74 |
| $C_2^=$ selectivity | 3.19 | 14.91 | 16.40 |
| $C_3^=$ selectivity | 5.41 | 21.36 | 22.93 |

[1]weight percent based on carbon

The data in Table 2 show the synergistic effects evident in the dual-function catalyst. Compared to the dehydrogenation catalyst alone, the combined catalyst raised cracked product yields of light olefins of ethylene and propylene. Yields of ethylene and propylene from the combined catalyst were higher than the combined yields for each individual component.

Example 3

This example illustrates the use of SAPO-type solid acid components for combined oxydehydrogenation/acid cracking. In each case, 1 g of Component C prepared in Example 1 was mixed with either OlefinsMax, SAPO-34, or SAPO-11. The oxydehydrogenation/cracking of n-butane was studied in a downflow, fixed-bed, pulse-type reactor at 550° C. The catalysts were mixed with SiC to obtain constant bed heights and then pretreated in a helium stream at a flow rate of 50 cc/min for thirty minutes at 550° C. and one atmosphere prior to reaction. At the start of the reaction, the helium flow was sent to a bypass and a pulse of 0.5 g of n-butane flowing at a rate of 50 cc/min was introduced into the system. Once the 0.5 g of n-butane was delivered, the helium flow was redirected to the reactor system. The pressure during reaction was 4–5 psig. Table 3 shows the results for the combined catalysts consisting of different solid acid components. Two grams of each catalyst was charged to the reactor. The data in Table 3 show that a synergistic effect is still evident between the SAPO structures and the metal-based component as a result of the low butadiene yields. The SAPO structures lead to significantly lower yields of the less desirable ethane and propane as well as to significantly lower aromatics yields.

TABLE 3

| (Cwt %) | Component C (1 g) OlefinsMax (1 g) | Component C (1 g) SAPO-34 (1 g) | Component C (1 g) SAPO-11 (1 g) |
|---|---|---|---|
| $C_4$ conversion | 26.43 | 24.66 | 20.45 |
| $C_4^=$ yield | 3.97 | 4.90 | 6.19 |
| $C_4^{==}$ yield | 0.06 | 0.37 | 0.32 |
| CO yield | 0.61 | 1.36 | 1.40 |
| $CO_2$ yield | 2.08 | 3.90 | 4.26 |
| $C_1$ yield | 1.42 | 0.85 | 0.85 |
| $C_2^=$ yield | 3.94 | 3.60 | 1.75 |
| $C_2$ yield | 2.65 | 0.66 | 1.13 |
| $C_3^=$ yield | 5.65 | 6.53 | 2.92 |
| $C_3$ yield | 2.57 | 1.35 | 0.14 |
| Benzene yield | 0.84 | 0.23 | 0.40 |
| Toluene yield | 1.34 | 0.08 | 0.49 |
| $C_{5+}$ (non-aromatic) | 1.32 | 0.83 | 0.61 |
| $C_4^=$ selectivity | 15.01 | 19.86 | 30.27 |
| $C_4^{==}$ selectivity | 0.23 | 1.50 | 1.54 |
| CO selectivity | 2.30 | 5.50 | 6.86 |
| $CO_2$ selectivity | 7.85 | 15.82 | 20.81 |
| $C_2^=$ selectivity | 14.91 | 14.60 | 8.55 |

Example 4

This example illustrates the benefits of the inventive catalyst with an n-hexane feed. The oxydehydrogenation/cracking of n-hexane was studied in a downflow, fixed-bed reactor at 550° C. The catalyst was pretreated in a helium stream at a flow rate of 100 cc/min (cubic centimeters per minute) for thirty minutes at 550° C. and one atmosphere prior to reaction. N-hexane was fed at a flow rate of 0.176 g/min. The pressure during reaction was 4–5 psig (pounds per square inch gauge). Three catalysts were tested: 1 g of Component C as described in Example 1, a mixture of 1 g of Component C and 1 g of SAPO-34, and 1 g of SAPO-34. Table 4 lists the products distribution for three different catalyst charges. Component C alone leads to a large yield of the undesirable benzene product, whereas the solid acid alone produces a low conversion and low yields to the desired ethylene and propylene products. The mixed catalyst, however, leads to a higher conversion with increased yields of ethylene, propylene and butylenes that are higher than the sum of the yields of the individual components. A lower yield of benzene is also obtained, indicating that the formation of benzene is interrupted in favor of the formation of the desirable light olefins.

TABLE 4

| Catalyst Description. | Component C (1 g) | Component C (1 g) & SAPO-34 (50/50) | SAPO-34 |
|---|---|---|---|
| Catalyst amount (g) | 1 | 2 | 1 |
| n-$C_6$ feed (ml/min) | 0.267 | 0.267 | 0.267 |
| amount oil fed (g) | 0.0619 | 0.0513 | 0.0507 |
| WHSV[2] | 10.50 | 5.25 | 10.50 |
| Catalyst/Oil | 16.15 | 39.01 | 19.72 |
| Product (Cwt %)[1] | | | |
| $C_1$ | 1.04 | 1.64 | 0.68 |
| $C_2^=$ | 2.01 | 9.17 | 1.51 |
| $C_2$ | 1.10 | 1.70 | 0.92 |
| $C_3^=$ | 1.82 | 23.92 | 3.61 |

TABLE 4-continued

| Catalyst Description. | Component C (1 g) | Component C (1 g) & SAPO-34 (50/50) | SAPO-34 |
|---|---|---|---|
| $C_3$ | 0.23 | 2.53 | 0.86 |
| $C_4^{--}$ | 0.29 | 0.98 | 0.64 |
| $C_4^-$ | 0.53 | 2.65 | 1.55 |
| $C_4$ | 0.12 | 0.46 | 0.58 |
| $C_5$'s | 0.33 | 0.67 | 0.65 |
| i-$C_6$ & $CYC_6$[3] | 0.75 | 0.25 | 0.02 |
| $C_6^-$ | 4.35 | 1.28 | 0.62 |
| $C_6$ | 31.30 | 36.79 | 88.74 |
| Benzene | 44.50 | 3.42 | 0.09 |
| $C_7$'s | 0.03 | 0.04 | 0.01 |
| Toluene | 0.05 | 0.17 | 0.02 |
| $C_8$'s | 0.08 | 0.00 | 0.01 |
| $CO_2$ | 10.73 | 14.74 | 0.02 |
| Conversion | 68.70 | 63.21 | 11.26 |

Notes:
[1]PRODUCT CWT % = product stream composition, weight percent relative to carbon
[2]WHSV = weight hourly space velocity
[3]CYC6 = cyclic molecules containing 6 carbons, with the exclusion of benzene Example 5

A sample of Li—Mn oxides was prepared by first dissolving 10.0 g manganese(II) acetate tetrahydrate and 2.89 g lithium nitrate in 52.1 g of doubly deionized water. The resulting solution was stirred and heated until water was evaporated and the sample was dry. The resulting solid was dried at 120° C. for 6 hours, followed by calcination at 700° C. for 12 hours, with a heating rate of 10° C./min.

The combined catalyst was prepared by physically mixing ground powders on the basis of 75 weight % (wt %) Li—Mn oxide and 25 wt % SAPO-34 zeolite. The mixed catalyst powders were pelletized and screened to 60–100 mesh particles. A second catalyst was prepared by mixing 75 wt % of Component B as shown in Table 1 and 25 wt % SAPO-34. The oxydehydrogenation/cracking of n-hexene was studied in a downflow, fixed-bed reactor at a n-hexene flow rate 0.088 g/min and 550° C. and 4–5 psig. In each test, a mixture of 0.5 g of catalyst and 3.0 g of SiC were charged to the reactor. The catalysts were pretreated in a helium stream at a flow rate of 100 cc/min for thirty minutes at 550° C. and 1 atmosphere pressure prior to reaction. As shown in Table 5, both Component B and Li—Mn oxides as the metal-based component raised conversion and yields of ethylene, propylene, and butylenes. Benzene yields are also decreased.

TABLE 5

| Catalyst Description | Component B/ SAPO-34 (75/25) (75%/25% by wt) | $Li_2MnO_4$/ SAPO-34 (75%/25% by wt.) |
|---|---|---|
| catalyst amount (g) | 0.5 | |
| n-$C_6$ feed (ml/min) | 1.33 | 1.33 |
| Temperature (° C.) | 550.00 | 550.00 |
| amount oil fed (g) | 0.0572 | 0.0451 |
| WHSV | 104.80 | 104.80 |
| Catalyst/Oil | 8.73 | 11.09 |
| Product (Cwt %) | | |
| $C_1$ | 0.45 | 1.10 |
| $C_2^-$ | 2.49 | 4.24 |
| $C_2$ | 0.55 | 1.01 |
| $C_3^-$ | 11.75 | 13.57 |
| $C_3$ | 0.60 | 0.51 |
| 1,3 $C_4^-$ | 0.21 | 0.28 |
| $C_4^-$ | 2.10 | 2.24 |
| $C_4$ | 0.15 | 0.11 |
| $C_5$ | 0.62 | 0.61 |
| i-$C_6$ and $CYC_6$ | 0.34 | 0.19 |
| $C_6^-$ | 3.10 | 1.87 |
| $C_6$ | 73.75 | 52.20 |
| Benzene | 1.42 | 0.51 |
| $C_7$ | 0.06 | 0.02 |
| Toluene | 0.13 | 0.06 |
| $C_8$ | 0.11 | 0.07 |
| $CO_2$ | 1.91 | 21.40 |
| CO | 0.26 | 0.02 |
| Conversion | 26.25 | 47.80 |

Example 6

A sample of Sm—V oxides was prepared by first dissolving 14.3 g samarium(III) acetate trihydrate and 4.46 g ammonium metavanadate in 100.2 g of doubly deionized water. The solution was stirred and concentrated aqueous ammonia was added until a pH of 10 was attained. The resulting slurry was stirred and heated until water was evaporated and the sample was dry. The sample was then calcined at 550° C. for 6 hours and 700° C. 10 hours, with a heating rate of 10° C./min. The combined catalyst was prepared by physically mixing ground powders of 75 wt % the Sm—V oxides and 25 wt % SAPO-34. The mixed catalyst powders were pelletized and screened to 60–100 mesh particles. The oxydehydrogenation/cracking of n-hexane was studied in a downflow, fixed-bed reactor at 600° C. The catalyst was pretreated in a helium stream at a flow rate of 100 cc/min for thirty minutes at 600° C. and one atmosphere prior to reaction. N-hexane was fed at a flow rate of 0.88 g/min. The pressure during reaction was 4–5 psig. Test results are shown in Table 6. Sm—V oxides as the metal-based component leads to good light olefins yield and a significant decrease in the production of $CO_x$ during oxydehydrogenation/cracking.

TABLE 6

| Catalyst description | Component B/SAPO-34 (75%/25% by wt.) | Sm-V/SAPO-34 (75%/25% by wt.) |
|---|---|---|
| Catalyst amount (g) | 0.5006 | 0.5009 |
| n-$C_6$ feed (ml/min) | 1.33 | 1.33 |
| Temperature (C.) | 598 | 600 |
| amt oil fed (g) | 0.1530 | 0.1470 |
| WHSV | 105.21 | 105.15 |
| Cat./Oil | 3.27 | 3.41 |
| sample # | 4 | 5 |
| Product (Cwt %) | 1 | 1.08 |
| $C_1$ | 2.25 | 2.53 |
| $C_2^-$ | 6.20 | 4.63 |
| $C_2$ | 2.55 | 3.47 |
| $C_3^-$ | 16.89 | 11.44 |
| $C_3$ | 1.19 | 1.33 |
| 1,3 $C_4^-$ | 0.62 | 0.33 |
| $C_4^-$ | 3.13 | 3.71 |
| $C_4$ | 0.31 | 0.36 |
| $C_5$s | 1.12 | 1.39 |
| i-$C_6$ and CYC6 | 0.35 | 0.36 |
| $C_6^-$ | 2.65 | 2.56 |
| $C_6$ | 54.57 | 63.69 |
| Benzene | 2.87 | 3.49 |
| $C_7$s | 0.09 | 0.06 |

TABLE 6-continued

| Catalyst description | Component B/SAPO-34 (75%/25% by wt.) | Sm-V/SAPO-34 (75%/25% by wt.) |
|---|---|---|
| Toluene | 0.20 | 0.25 |
| $C_8s$ | 0.13 | 0.20 |
| $CO_2$ | 4.86 | 0.19 |
| CO | 0.03 | 0.01 |
| Conversion | 45.43 | 36.31 |

Example 7

This example illustrates the preparation and testing of a catalyst consisting of a metal-based component, a solid acid component and a binder component of Bentonite clay. The catalyst was prepared by first physically mixing ground powders of 1.5 g of Component B from Example 1 and 0.5 g of SAPO-34. 2 g of Bentonite clay was added to this well mixed powder of Component B and SAPO-34 and the resulting mixture of Bentonite, Component B, and SAPO-34 was mixed thoroughly. Ethanol was then added in an amount necessary to form a paste and this resulting paste was thoroughly mixed. The paste was pelletized under low pressure to form a cake. The cake was dried at 110° C. for 12 hours and then heated at 1° C./min to 400° C. and calcined at this temperature for 8 hours. After cooling, the cake was crushed and sieved into 60–100 mesh particles. The oxydehydrogenation/cracking of n-hexane was studied in a downflow, fixed-bed reactor at 550° C. 1.0 grams of catalyst was mixed with 6 g of SiC. The catalyst was pretreated in a helium stream at a flow rate of 100 cc/min for thirty minutes at 550° C. and one atmosphere pressure prior to reaction. N-hexane was fed at a flow rate of 1.33 g/min. The pressure during reaction was 4–5 psig. Test results are shown in Table 7. The catalyst comprised of Component B, SAPO-34, and Bentonite produces a 27.04 wt % based on carbon conversion of n-hexane feed. Yields of the desired ethylene and propylene products are 2.42 and 11.97 wt %, respectively.

TABLE 7

| Catalyst Amount (g) | 1 |
|---|---|
| n-$C_6$ feed (ml/min) | 1.33 |
| amount oil fed (g) | 0.0620 |
| WHSV | 52.40 |
| Catalyst/Oil | 15.90 |
| Product (Cwt %) | |
| $C_1$ | 0.43 |
| $C_2^=$ | 2.42 |
| $C_2$ | 0.55 |
| $C_3^=$ | 11.97 |
| $C_3$ | 0.60 |
| $C_4^{==}$ | 0.23 |
| $C_4^=$ | 1.98 |
| $C_4$ | 0.15 |
| $C_5s$ | 0.55 |
| i-$C_6$ & $CYC_6$ | 0.33 |
| $C_6^=$ | 3.15 |
| $C_6$ | 72.96 |
| Benzene | 2.50 |
| $C_7s$ | 0.04 |
| Toluene | 0.11 |
| $C_8s$ | 0.08 |
| $CO_2$ | 1.91 |
| CO | 0.04 |
| n-$C_6$ Conversion | 27.04 |

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process comprising contacting a paraffinic hydrocarbon feed stream with an oxydehydrogenation/cracking catalyst under suitable catalytic reaction conditions and catalytically oxydehydrogenating and cracking paraffins to produce olefins, wherein said paraffinic hydrocarbon feedstream is fed in an anaerobic manner to said oxydehydrogenation/cracking catalyst comprising at least one molecular sieve cracking component selected from ZSM-5, SAPO-34, and SAPO-11 and at least one oxydehydrogenation component to oxydehydrogenate and crack the paraffinic hydrocarbon to produce olefins.

2. The process of claim 1 wherein said oxydehydrogenation catalyst comprises one or more elements from Groups 1–3, one or more elements from Groups 4–15 and one or more elements from Groups 16 and 17 of the Periodic Table of the Elements.

3. The process of claim 1 wherein catalytic cracking is conducted in the substantial absence of added heat.

4. The process of claim 1 wherein said paraffinic hydrocarbon feedstream comprises butane, hexane, or a mixture thereof and said olefins produced comprise propylene.

5. The process of claim 1, wherein anaerobic oxydehydrogenation is conducted using the lattice oxygen in the catalyst as the oxygen source and at least one regenerator is used to reactivate the spent catalyst and to replenish the consumed lattice oxygen.

6. The process of claim 1 wherein the process generates heat.

7. The process of claim 1, wherein the process produces water as a by-product.

8. The process of claim 1, wherein said olefins comprise ethylene and propylene.

9. The process of claim 1, wherein said feedstream is selected from at least one of steam cracked gas oil and residues, gas oils, heating oil, jet fuel, diesel, kerosene, gasoline, coker naphtha, steam cracked naphtha, catalytically cracked naphtha, hydrocrackate, reformate, raffinate reformate, Fischer-Tropsch liquids, Fischer-Tropsch gases, natural gasoline, distillate, virgin naphtha, $C_{5+}$ olefins (i.e., $C_5$ olefins and above), $C_{5+}$ paraffins, ethane, propane, butanes, butenes, butadiene, and mixtures thereof and said olefins produced comprise propylene.

10. The process of claim 2, wherein the element(s) from Groups 1–3 is (are) at least one of lithium, sodium, potassium, magnesium, calcium, barium, lanthanum, samarium and yttrium.

11. The process of claim 2, wherein the element(s) from Groups 1–3 is (are) at least one of magnesium and calcium.

12. The process of claim 2, wherein the element from Groups 1–3 is magnesium.

13. The process of claim 2, wherein the element(s) from Groups 4–15 is (are) at least one of vanadium, titanium, chromium, manganese, iron, cobalt, nickel, copper, zinc, zirconium, molybdenum, cadmium, hafnium, tantalum, tungsten, osmium, niobium, iridium, bismuth and platinum.

14. The process of claim 2, wherein the element from Groups 4–15 is vanadium.

15. The process of claim 2, wherein the elements(s) from Groups 16 and 17 is (are) at least one of oxygen, fluorine, sulfur, chlorine, bromine, and iodine.

16. The process of claim 2, wherein the elements from Group 16 and 17 is oxygen.

17. The process of claim 2, wherein said oxydehydrogenation component comprises magnesium, vanadium, and oxygen.

18. The process of claim 1, wherein said feedstream is fed to said catalyst at the rate of at least one million kilograms per day.

19. The process of claim 1, wherein said catalyst comprises said molecular sieve cracking component and a vanadium-based oxydehydrogenation component further comprising magnesium and oxygen.

* * * * *